United States Patent [19]

Leopardi

[11] 4,361,536
[45] Nov. 30, 1982

[54] METHOD FOR STERILIZING CONTACT LENSES

[75] Inventor: Stefania Leopardi, Rome, Italy

[73] Assignee: Industrie Ottiche Riunite S.p.A., Marghera-Venezia, Italy

[21] Appl. No.: 236,928

[22] Filed: Feb. 23, 1981

[30] Foreign Application Priority Data

Feb. 25, 1980 [IT] Italy ............................... 20157 A/80

[51] Int. Cl.³ .............................................. A61L 2/20
[52] U.S. Cl. ......................................... 422/33; 134/6; 422/39; 422/297
[58] Field of Search ..................... 422/28, 33, 39, 300, 422/297; 134/6; 15/320, 97 R

[56] References Cited

U.S. PATENT DOCUMENTS

| | | | |
|---|---|---|---|
| 1,728,333 | 9/1929 | Crowther | 422/39 |
| 1,728,334 | 9/1929 | Crowther | 422/39 X |
| 1,983,648 | 12/1934 | Warth | 422/33 |
| 3,168,100 | 2/1965 | Rich | 422/300 X |
| 3,519,005 | 7/1970 | Krezanoski | 134/143 |
| 4,169,123 | 9/1979 | Moore et al. | 422/33 X |
| 4,187,574 | 2/1980 | Wrue | 15/97 R X |
| 4,230,663 | 10/1980 | Forstrom et al. | 422/33 |

*Primary Examiner*—Barry S. Richman
*Attorney, Agent, or Firm*—Diller, Ramik & Wight

[57] ABSTRACT

A method and apparatus for sterilization of contact lenses characterized in that the lenses are enclosed in the interior of a sealtight chamber having rigid and indeformable walls, the following sequence of steps being performed:

(a) introducing in said chamber a carbon dioxide stream;
(b) producing a vacuum in the interior of said chamber, and
(c) filling said chamber with carbon dioxide until a preselected pressure is attained.

8 Claims, 2 Drawing Figures

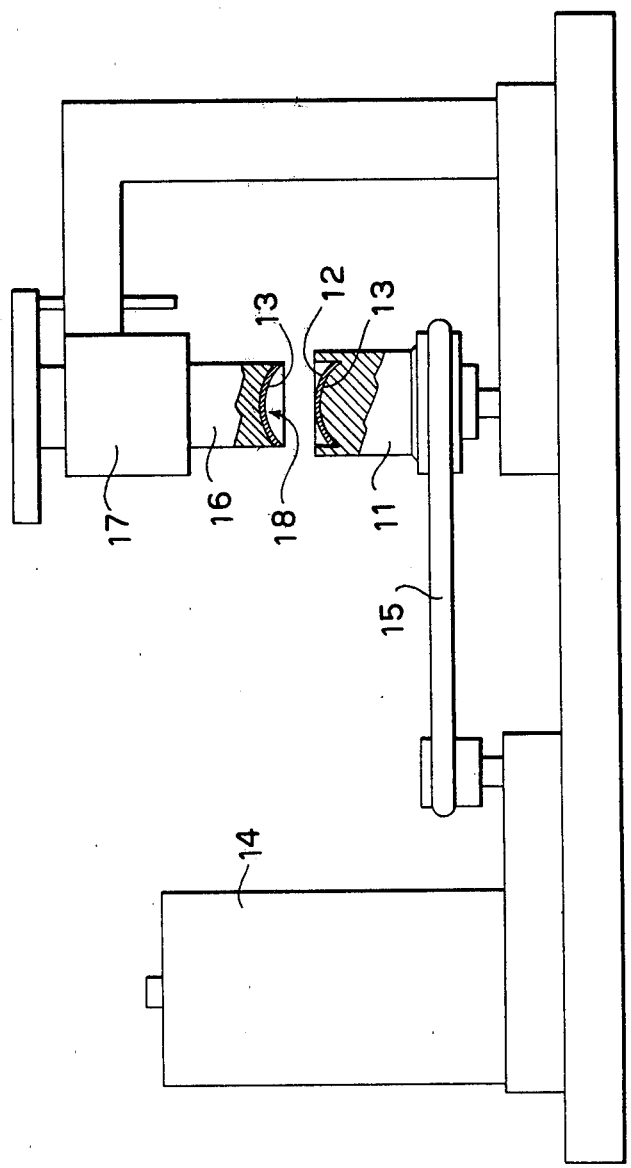

METHOD FOR STERILIZING CONTACT LENSES

A contact lens is regarded as being biologically sterile when it does not contain any living form of obligate aerobic and anaerobic bacteria.

Up to the present days, for sterilizing contact lenses methods have been employed of exposures to dry or moist heat. It is known, for example, to sterilize contact lenses in specially provided boilers. In this connection one could be led to directly transferring to the field of the contact lenses the most common sterilization processes which employ heat, such as those using steam under pressure in an autoclave. However, the materials of which the lenses are made are incapable of withstanding the high temperatures involved in such treatments.

A few types of lenses, such as the soft lenses, even if they seemingly withstand heat treatments at high temperatures, actually, if subjected to repeated treatments of that kind, are irreversibly altered and lose a few of their most appreciable properties.

As a rule, the heat sterilization processes, including those in which temperatures below those characteristic of the autoclave methods, such as the sterilization in steam stream, have, on the other hand, the serious drawback that they are entirely inactive towards a number of heat-resistant bacterial species: in this connection, it should be considered, also, that a few bacteria, even if they are not inherently heat-resistant, may however acquire heat resistance under certain environmental conditions, for example as when they are occluded in the lipoid drops of the lacrimal film.

The inactivity towards the heat-resistant bacteria along with the thermolabile character of the materials the lenses are made of are, consequently, apparent limits against the applicability of the sterilization processes based on heat application to contact lenses.

In addition, may it be recalled that it is known to sterilize plastics material articles by using, in an autoclave, ethylene oxide, either as such or combined with $CO_2$, the latter gas reducing the flammability of ethylene oxide; it could thus be envisaged to sterilize also contact lenses by such a process. It should be considered, however, that there are general problems connected with such a process, which are the hazard of using such a gas and the necessity of extending the treatment for a long time in order that it may be efficient. Such a process is still less applicable to the field of contact lenses on account of the toxicity of the gas employed, the processing costs and the difficulty in carrying it into actual practice because, as outlined above, it must be carried out in an autoclave.

Still more widespread is the sterilization of contact lenses with chemicals used as bactericides, such as benzalconium chloride.

The latter process, while affording advantages over the heat sterilization methods, such as a greater practicability, is not capable of acting in a complete way on the spectrum of the bacteria which are present in the atmosphere.

In addition, such chemicals might not be easily tolerated by all lens wearers, due to the possible occurrence of allergy originated by cytotoxic states.

This is confirmed also by the fact that, in several countries, there are sanitary regulations which prohibit the use of such chemicals as sterilizing agents.

Another shortcoming of such chemicals is the occurrence of instability of their chemical and pharmaceutical properties with the lapse of time.

An object of the present invention is thus to achieve an efficient sterilization of contact lenses capable of solving the problems outlined above which are inherent in the conventional sterilization processes.

For efficient sterilization it is intended herein a sterilization which is such as to prove active on the widest possible field of bacterial species, including the heat-resistant ones.

An object of the invention is also to make possible the practical performance of an efficient sterilization, so that the process may readily be carried out, especially for being applied to the sterilization of contact lenses, also by unskilled persons.

Another object of this invention is then to provide a device for sterilizing contact lenses, said device being practical and simple in use and also conveniently movable from a place to another as a function of the requirements of use of the lenses concerned.

In order that such objects may be achieved, this invention provides a method for sterilizing contact lenses which is characterized in that it comprises the steps of introducing the lenses into the interior of a sealtight chamber having rigid and undeformable walls, whereafter the following sequence of stages is performed:

(a) introducing a carbon dioxide stream into said chamber;

(b) producing a vacuum in the interior of said chamber, and (c) filling said chamber with gaseous carbon dioxide until a preselected pressure value is attained.

According to a preferred embodiment of the method according to this invention, prior to carrying out the sequence of operations outlined in the preceding paragraph, the contact lenses are mechanically washed with any appropriate detergent.

Obviously, such a washing step can also carried out manually, according to the simple procedures which are well known to all contact lens users.

This invention also relates to an apparatus which is adapted to carry out the process according to the invention, said apparatus being essentially comprised of a chamber having rigid and undeformable walls so that a gas stream may be fed thereinto and maintained under pressure therein for a preselected period of time, means for positioning the lenses in the interior of said chamber, means for feeding in said gas, means for producing a vacuum in the interior of said chamber.

Whenever the sterilization process provides also for the prewashing stage aforementioned, the apparatus provided herein is also equipped with means for carrying out said prewashing step.

In order that the method and the apparatus according to the invention may be best understood, an example of the best mode to carry out the method and to embody the machine of this invention will be given hereinafter without limitation, the descriptive part being illustrated by the accompanying drawings, wherein:

FIG. 2 is a diagrammatical detail view of the machine that is a device for mechanically prewashing contact lenses.

Figure 1:
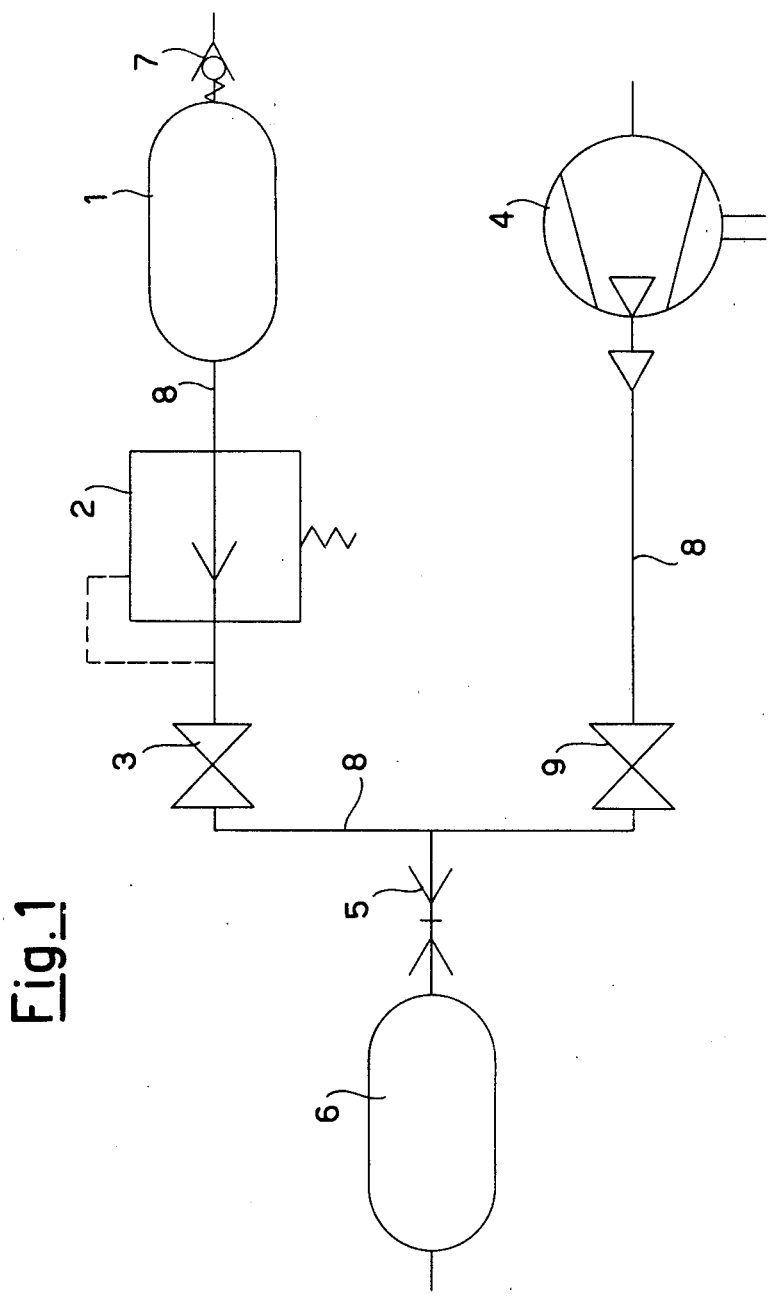
FIG. 1 is a block diagram of an apparatus according to the invention.

Reference being had, at the outset, to FIG. 1, a sterilization chamber, 6, is connected, via a sealtight circuitry (fluid) diagrammatically outlined by the line 8, to a $CO_2$ bottle 1, and to a vacuum pump 4. The bottle 1 has, on its top, a one-way valve 7 (non-return valve) for periodically reloading the bottle. At its outlet, the bottle has a pressure reducing unit 2 which enables a constant gas stream to be dispensed by the container 1 to the chamber 6. Between the bottle 1 and the chamber 6 there are provided a stop-cock 3 for cutting off the gas stream and a valve 5 for quick connection of the circuitry 8 to the chamber 6. A stop-cock 9 is likewise provided for disconnecting the vacuum pump 4 from the fluid circuitry 8.

Once the contact lenses to be sterilized have been positioned within the chamber 6, the sterilization chamber 6 is fed with $CO_2$ coming from the bottle 1, until the latter is emptied. By way of example only, the $CO_2$ pressure in the interior of the chamber 6 on completion of the gas supply is about 1.5 atm.

Once the entire change of $CO_2$ has been introduced into the chamber 6, the vacuum pump 4 is started, to produce a vacuum within the chamber 6 until the value of the negative pressure is for example between 50 and 60 mmHg. The time during which such a degree of vacuum is maintained is about one minute. Thereafter, the bottle 1 is reloaded with $CO_2$ and the chamber 6 is filled with carbon dioxide again until a pressure of about 1.5 atm is attained again in the interior of the chamber. This $CO_2$ environmental pressure is maintained for a minimum time of 20 minutes approximately.

At any rate, the contact lenses are allowed to stand in the $CO_2$ environment under pressure in the interior of the chamber 6 up to the instant of use.

The apparatus shows diagrammatically in FIG. 1 is enclosed within a casing, which is preferably metallic and portable, and which is fitted with appropriate housings adapted to hold each of the component parts of the chamber.

FIG. 2 diagrammatically shows a device for the mechanical washing of contact lenses; said device is preferably arranged in the interior of the apparatus described hereinbefore and within a specially provided casing. The device is comprised of a cylindrical housing 11, shown in the drawing partly in cross-section, equipped with a top base or base piece 12 having a convex curved surface adapted to receive a contact lens to be treated. The base piece 12 has superposed thereto a filter 13, also with a convex outline, so as to match said base 12 and made of a porous soft material, for example a soft filter paper of high porosity rating adapted to absorb capillarly a detergent liquid for contact lenses and intended directly to support the contact lens concerned. Said housing 11 may have a rotary motion axially impressed thereto by a small motor 14 which drives the housing 11 via a belt drive 15 connected thereto.

The housing 11 cooperates with a cylindrical complementary housing 16, having a lower curved base 18 of curved outline complementary to the surface of the base 12 of the housing 11. The housing 16 can slide within a fixed seating 17 in the axial direction so that it can be approached to the housing 11 until abutting the top base of said housing 11 snugly.

On the curved base 18 of housing 16 there is positioned a second special filter 13, soaked with a liquid detergent.

In the drawing, the two housings 11 and 16 are shown in the spaced apart position which permits the positioning of a contact lens therebetween, by having the lens to be cleaned placed on the filter 13 resting on the base 12 of the housing 11.

Once the filters 13 have been soaked with a liquid detergent and the lens to be cleaned is placed to rest on the filter of the housing 12, the complementary housing 16 is approached to the housing 11.

The device is thus in its working position. Washing is carried out by energizing the motor 14 so that the housing 11 is driven to rotation. In the working position, the two filters 13, soaked with liquid, stick to the two opposite surfaces of the lens simultaneously.

The rotary motion of the lower filter relative to the upper filter, the latter being in a position fixed in space, ensures quite satisfactory a cleaning of the lens pinched therebetween. To this purpose, the washing device might have, associated therewith, a liquid detergent feeding system of conventional make for feeding the liquid detergent continuously to the filters.

The mechanism of action of the sterilization process provided by the present invention might be explained, in its essentials, as follows:

The introduction in the interior of the chamber of a gaseous $CO_2$ stream in the first stage a) of the process described herein, brings about the establishing of an atmosphere of such gas which, maintained under preselected conditions of temperature and pressure and during a likewise preselected time, is capable of selectively acting upon the metabolic processes of the bacterial cells and thus of inducing modifications in their structure.

More particularly, the introduction of $CO_2$ until attaining a preselected pressure within the chamber according to stage (a) of the process in question, has the task of bringing about an initial deactivation of the bacteria which are present, and, in quite selective a way, of the aerobic bacteria.

During said stage (a) the bacterial cells are thus, as a rule, subjected to a gaseous atmosphere capable of acting thereupon in a biologically selective manner: such a gas, moreover, imparts a pressure onto the cell walls.

During the subsequent stage (b), instead a vacuum is rapidly provided in the chamber interior and the sudden transition from conditions of positive pressure to molecular vacuum conditions has the effect of subjecting the cellular membranes to a considerable strain.

Microorganisms, in general, have proven to be incapable of withstanding a physical stress of that kind: it can be surmised, therefore, that on that occasion, and especially in correspondence with certain active sites of the cellular membrane, a breakdown of the membrane is experienced, with an attendant spurting of intracellular material, the result being the deactivation of any bacterial activity whatsoever.

Summing up, it can be stated that the production and the maintenance of a vacuum in the interior of the chamber produces the effect of modifying the surface tension of the material subjected to sterilization. It is however extremely difficult to explain the exact mechanism by which such a phenomenon display a bacteriostatic or a bactericidal action: it should be considered, for example, that the variation of the surface tension at the contact surface between the liquid (i.e. the solution to be sterilized) and the gas is sharply different from that between the cellular wall and the surrounding liquid.

The ultimate stage of the method provided herein simultaneously effects a final "scrubbing" of the contact lens and a selective deactivation of the aerobic bacteria which are present, in a virtually total absence of the air which was initially contained in the chamber.

I claim:

1. A method of sterilizing contact lenses characterized in that it comprises the steps of introducing said lenses in the interior of a sealtight chamber having rigid and undeformable walls, the following sequence of steps being performed:
    (a) introducing in said chamber a carbon dioxide stream to establish therein a predetermined superatmospheric pressure;
    (b) producing a vacuum in the interior of said chamber, and
    (c) filling said chamber with carbon dioxide until a preselected superatmospheric pressure value is attained, said preselected pressure value being maintained for a period of time to affect sterilization of said lenses.

2. A method according to claim 1, characterized in that said lenses are subjected to a washing step prior to being treated according to the processing stages as claimed in claim 1.

3. The method as defined in claim 1 wherein the preselected pressure value of step (c) is maintained for a minimum time of approximately 20 minutes.

4. The method as defined in claim 1 wherein the preselected pressure value of step (c) is approximately 1.5 atmosphere.

5. The method as defined in claim 1 wherein the vacuum of step (b) is maintained for approximately one minute.

6. The method as defined in claim 5 wherein the preselected pressure value of step (c) is approximately 1.5 atmosphere.

7. The method as defined in claim 5 wherein the preselected pressure value of step (c) is maintained for a minimum time of approximately 20 minutes.

8. The method as defined in claim 7 wherein the preselected pressure value of step (c) is approximately 1.5 atmosphere.

* * * * *